United States Patent
Harish et al.

(10) Patent No.: US 8,705,823 B2
(45) Date of Patent: Apr. 22, 2014

(54) SOFTWARE PRODUCT FOR BREAST EXAMINATION RESULT MAPPING, RECORDING, COMPARING, AND/OR TRACKING

(75) Inventors: Ziv Harish, Tenafly, NJ (US); Isaac Rubinstein, Haworth, NJ (US); Ehud Arbit, Englewood, NJ (US); Russ Weinzimmer, Milford, NH (US)

(73) Assignee: Newel Dexter LLC, Tenafly, NH (US)

( * ) Notice: Subject to any disclaimer, the term of this patent is extended or adjusted under 35 U.S.C. 154(b) by 178 days.

(21) Appl. No.: 13/152,129

(22) Filed: Jun. 2, 2011

(65) Prior Publication Data
US 2012/0308094 A1 Dec. 6, 2012

(51) Int. Cl.
G06K 9/00 (2006.01)

(52) U.S. Cl.
USPC .......................................... 382/128

(58) Field of Classification Search
USPC ................. 382/128–134; 128/920–925; 600/407–414, 424–426; 345/581–618
See application file for complete search history.

(56) References Cited

U.S. PATENT DOCUMENTS

| | | | |
|---|---|---|---|
| 5,207,582 A | 5/1993 | Michelson | |
| 5,657,753 A | 8/1997 | Jacober et al. | |
| 5,913,686 A | 6/1999 | VanWinkle | |
| 6,119,033 A * | 9/2000 | Spigelman et al. | 600/426 |
| 6,179,786 B1 | 1/2001 | Young | |
| 6,419,636 B1 | 7/2002 | Young et al. | |
| 6,575,903 B1 | 6/2003 | Collins | |
| 6,595,933 B2 | 7/2003 | Sarvazyan et al. | |
| 6,669,650 B1 | 12/2003 | Anker et al. | |
| 6,685,651 B2 | 2/2004 | Anker et al. | |
| 6,970,827 B2 | 11/2005 | Zeltzer et al. | |
| 2003/0120515 A1 | 6/2003 | Geller | |
| 2004/0254503 A1* | 12/2004 | Sarvazyan et al. | 600/587 |
| 2005/0152588 A1* | 7/2005 | Yoshida et al. | 382/128 |
| 2010/0022881 A1* | 1/2010 | Fujita et al. | 600/445 |

FOREIGN PATENT DOCUMENTS

WO 2005027744 A1 5/2003

OTHER PUBLICATIONS

Google Document 1 downloaded on Oct. 19, 2010. www.breastcancer.org.
Google Document 2 downloaded on Oct. 19, 2010. http://rushprnews.com/2010/09121/new-iphone-app-helps-raise-breast-awareness.
Google Document 3 downloaded on Oct. 19, 2010. http://apps.bitwiseanalytics.com/tnm-breast/.
Google Document 4 downloaded on Oct. 19, 2010. http://www.ibreastcheck.com/.

(Continued)

*Primary Examiner* — Atiba O Fitzpatrick
(74) *Attorney, Agent, or Firm* — Russ Weinzimmer & Associates, P.C.

(57) ABSTRACT

A breast examination system is disclosed that facilitates normalized quantitative comparison of results from multiple examinations performed under differing conditions, such as different viewing angles. The proposed system can operate on a camera-equipped smart-phone, a camera-equipped desktop computer, or on a dedicated device to perform a guided breast cancer examination, and then store results of the examination in a normalized format that allows effective quantitative comparison to historic results, thereby detecting changes and trends. The results can be stored on the local device, or on a web-based server, providing various data comparison, data management, and data interpretation services in a secure and controlled manner.

20 Claims, 17 Drawing Sheets

(56) References Cited

OTHER PUBLICATIONS

Google Document 5 downloaded on Oct. 19, 2010. http://www.imedappsteam.com/iMedAppsTeam/Home.html.

Google Document 6 downloaded on Oct. 19, 2010. http://www.mammacare.com/learning_systems.php.

Google Document 7 downloaded on Oct. 19, 2010. http://www.ideallifeonline.com/newsroom/Medtec_Insight_-_Consumer_and_Clnical_Markets_Merge_-_Aug._2009_Page10.pdf.

* cited by examiner

SOFTWARE PRODUCT FOR BREAST EXAMINATION RESULT MAPPING, RECORDING, COMPARING, AND/OR TRACKING

FIELD OF THE INVENTION

This invention relates generally to breast examination, and more particularly to breast examination result management and interpretation.

BACKGROUND OF THE INVENTION

The breasts are glands consisting of ducts embedded in fatty tissue. Breast cancer is considered to be the most commonly occurring cancer in middle-aged women. Breast cancer can arise anywhere in the duct system: from the nipple to the terminal lobule. Breast cancer is a potentially lethal disease, and the earlier it is detected, the more likely it can be successfully treated.

However, breast cancer is often detected only after it has spread to other parts of the body. Frequent breast exams are therefore essential for early identification and treatment. The breast self-exam should be performed as frequently as every month, immediately following the menstrual cycle.

Breast self-examination methods are well known. For example, most methods include visual inspection and tactile inspection:

Step 1—Visual Inspection

Look for changes in the skin over each breast—redness, swelling, or puckering.

Look for nipple changes—discharge, scaling, or indentation.

Step 2—Tactile Inspection

Physicians recommend using at least one of three tactile breast examination methods: The Circle method, The Line method, and The Wedge method.

The Circle Method includes moving the three middle fingers in an inward spiral pattern starting from the outer edge of the breast until the nipple is reached. The Line Method includes moving the three middle fingers in a raster pattern, starting from underarm area down below the breast, moving slowly back and forth until the entire breast is traversed. The Wedge method includes moving the three middle fingers beginning at the outer edge towards the nipple returning to the outer edge of the breast and repeating in a daisy pattern until the entire breast is felt.

Regardless of the method, the objective is to feel the entire breast and observe any changes. To self-examine one's breasts, a woman lies down and places one arm behind her head while using three middle fingers of her other arm to perform the examination. Note that the self-exam is done while lying down, not standing up. This is because when lying down, the breast tissue spreads evenly over the chest wall and is as thin as possible, making it much easier to feel all the breast tissue. The breast should feel soft and smooth to the touch. The woman must pay special attention to the underarm and upper chest areas. She must look for lumps as small as a pea, or as large as a grape.

Three different levels of pressure are used to feel tissue of the entire breast. Light pressure is needed to feel the tissue closest to the skin; medium pressure to feel a little deeper; and firm pressure to feel the tissue closest to the chest and ribs. It is normal to feel a firm ridge in the lower curve of each breast. The woman should tell her doctor if she feels anything else out of the ordinary. If she is not sure how hard to press, she should consult with her doctor or nurse. She should use each pressure level to feel the breast tissue before moving on to the next spot.

Manual methods of breast self-examination require that a woman remember her past findings, so that she can compare her current findings with her memory of past findings. However, this process of comparing with past findings based on her memory is a process that is both unreliable and not quantifiable.

Although the woman might attempt to make manual diagrams each time, and compare the diagrams, this method is not comprehensive, reliable, quantifiable, or reproducible.

Medical professionals performing breast examinations as well as women performing elf-examinations need an objective method to record their findings and compare finding of the current examination with results of examinations from the past.

SUMMARY OF THE INVENTION

The method of the invention allows a anyone performing a breast examination to take a picture of the breasts, mark lesions directly upon the picture of the breast, or directly upon the breasts, and then assist the examiner in normalizing the picture with the marks so as to provide a representation that facilitates reliable and consistent comparison of the markings over time, regardless of different cameras, different camera angles, different distances, and different breast positions.

The system does not need to store an actual picture of the breasts. The system stores multiple normalized data sets, and then performs a time-based comparison among the multiple normalized data sets.

The method converts findings into a consistent and quantifiable set of data that can be reliably compared to previous findings. Furthermore, the consistent representation of normalized data enables visual analysis by overlaying multiple normalized data sets.

The method enables representation of historic data sets on a current picture, even if the historic data set was acquired from a different picture. The method enables transfer of any data set from any prior examination onto any image or diagram representing any woman's breasts, regardless of differences in viewpoint among the pictures. The method enables representation of multiple data sets on any picture of any woman's breasts. For example, the method can be used to transfer any set of normalized data from prior breast examinations onto an image of a woman's breasts taken from a different viewpoint than the viewpoint used to perform the prior breast examinations.

Each data set does not contain any personal information, such as pictures of a breast. No names or identifying information is stored. No pictures of breasts are stored. Data regarding breast lesions and breast structure is meaningless without a picture of an individual woman's breast. Identical data will look very different when related to a picture of a breast of a different woman.

A physician can interpret any normalized data set, especially when in possession of historical data sets acquired from a patient, without the need for any pictures of the actual patient. The physician can use any image or diagram of a breast to interpret the data.

Lesion markings on the actual breast can be color-coded so as to distinguish between soft, medium and hard lesions.

A woman can mark the locations of lesions directly on her breasts, and then can take a picture of her marked breasts. The picture is then automatically analyzed to detect the markings, and to relate the markings to the picture.

The method can be implemented on a smartphone, such as an iPhone, a Droid, or other mobile computing device, such as an iPod Touch.

The method keeps personal breast examination data private by NOT storing it, thereby avoiding the need to encrypt the data.

The method enables distinguishing between new lesions, changed lesions, and existing lesions, based on objective comparison of present results to results of past examinations.

The method employs breast image normalization that transfers any image into a pre-defined coordinate system.

The invention can also alert the woman on a regular schedule of her need to perform her breast self-examination.

The method uses color coding and superimposition of lesion markers, thereby enabling comparison of previous findings to current findings in a way that is easier, more accurate, and more reproducible than non-digital methods.

The method makes it easy for a woman to compare breast examination results, which makes it more likely that a woman will perform the recommended breast self-examination on a regular basis and successfully discover changes.

A general aspect of the invention is a system for enabling mapping and recording of breast examination results. The system provides a method that includes: enabling visible characterization of found lesions in a digital image of a woman's breasts, the visible characterization indicating breast lesion information including at least one of: lesion location, lesion consistency, lesion smoothness, lesion shape, as can be discerned from manual examination of the woman's breast. The method also includes: determining a breast coordinate system for each breast, the breast coordinate system for each breast having a respective coordinate system origin; mapping the location of each found lesion into a respective breast coordinate system so as to provide coordinates of each found lesion; and enabling digital recording of the coordinates of each found lesion along with other breast lesion information.

In some embodiments, determining a breast coordinate system for each breast for use in lesion mapping includes: enabling finding each nipple within the digital image so as to provide nipple position information for each nipple.

In some embodiments, determining a breast coordinate system for each breast for use in lesion mapping includes: enabling determination of a top breast pair boundary line, a bottom breast pair boundary line, a left breast boundary line, a center line between the breasts, and a right breast boundary line within the digital image so as to provide a set of reference lines.

In some embodiments, the method further includes: retrieving breast lesion information.

In some embodiments, the method further includes: comparing breast lesion information between at least two different data sets of breast lesion information, those data sets resulting from two different examinations of the woman's breasts.

In some embodiments, the method further includes: normalizing the digital image using the breast coordinate system so as to provide a normalized digital image. In further embodiments, normalizing the digital image using the breast coordinate system includes: rotating the digital image so as to horizontally align the tops of the two breasts; angularly distorting the digital image by extending the shorter breast so as to horizontally align the bottoms of the two breasts, thereby making the two breasts appear to be of identical length; expanding digital image width to fit the image of the two breasts to a pre-determined width; expanding digital image height to fit the image of the two breasts to a pre-determined height; and equalizing width of each of the two breasts within the digital image of the two breasts. In other further embodiments, the method further includes: for each breast, distorting the digital image of each breast vertically and horizontally, without changing height and width of the digital image of each breast, so as to locate each nipple at the coordinate system origin of each breast.

In some embodiments, the method further includes: enabling presentation of normalized breast lesion information results from a breast examination on a representation of a breast.

In some embodiments, the method further includes: enabling presentation of breast lesion information resulting from at least one prior breast examination on an unrelated representation of a breast. In further embodiments, method further includes: enabling presentation of lesion information representation marks that are color-coded so as to indicate lesion characteristics.

In some embodiments, enabling visual characterization of found lesions in a digital image of a woman's breasts includes: enabling the woman to mark locations of lesions directly on her breasts before she acquires an image of her marked breast; automatically detecting the marks using image processing; and automatically relating the marks to the coordinate system of the image.

In some embodiments, mapping the location of each found lesion includes: defining an origin as (0,0) for each breast, and positioning each origin at the position of a nipple of each breast in the representation of the breast; defining the left side of each breast to be at $X=-100$ within the coordinate system, the scale of the left side of each breast being independent from the scale of the left side of the other breast; defining the right side of each breast to be at $X=+100$ within the coordinate system, the scale of the right side of each breast being independent from the scale of the right side of the other breast, and the scale of the right side of each breast being independent from the scale of the left side of the same breast; defining the bottom side of each breast to be at $Y=-100$ within the coordinate system, the scale of the bottom side of each breast being independent from the scale of the bottom side of the other breast, and independent of all scales in X; and defining the top side of each breast to be at $Y=+100$ within the coordinate system, the scale of the top side of each breast being independent from the scale of the top side of the other breast, and the scale of the top side of each breast being independent from the scale of the bottom side of the same breast, and independent of all scales in X.

In another general aspect, the invention is a system for enabling viewing of digitally recorded breast examination results. The system provides a method including: enabling retrieval of digital recordings of breast lesion information, including coordinates and other breast lesion information of each breast lesion; determining a breast coordinate system for each breast, the breast coordinate system for each breast having a respective coordinate system origin; mapping the coordinates of each breast lesion using the breast coordinate system for each breast to a representation of a breast so as to provide mapped breast lesion information; and enabling display of the mapped breast lesion information in conjunction with the representation of the breast.

In some embodiments, the breast lesion information includes at least one of: lesion location, lesion consistency, lesion smoothness, and lesion shape.

In some embodiments, enabling display of the breast lesion information includes: displaying the breast lesion information in conjunction with a representation of the breast, the representation of the breast being unrelated to a representation used to create the digital recordings of breast lesion information.

In some embodiments, mapping the coordinates of each breast lesion includes: defining an origin as (0,0) for each breast, and positioning each origin at the position of a nipple of each breast in the representation of the breast; defining the left side of each breast to be at X=−100 within the coordinate system, the scale of the left side of each breast being independent from the scale of the left side of the other breast; defining the right side of each breast to be at X=+100 within the coordinate system, the scale of the right side of each breast being independent from the scale of the right side of the other breast, and the scale of the right side of each breast being independent from the scale of the left side of the same breast; defining the bottom side of each breast to be at Y=−100 within the coordinate system, the scale of the bottom side of each breast being independent from the scale of the bottom side of the other breast, and independent of all scales in X; and defining the top side of each breast to be at Y=+100 within the coordinate system, the scale of the top side of each breast being independent from the scale of the top side of the other breast, and the scale of the top side of each breast being independent from the scale of the bottom side of the same breast, and independent of all scales in X.

Another aspect of the invention is a system for enabling viewing of digitally recorded breast examination results. The system provides a method including: enabling retrieval of digital recordings of breast lesion information, including coordinates and other breast lesion information of each breast lesion; and enabling display of the breast lesion information.

In some embodiments, the breast lesion information includes at least one of: lesion location, lesion consistency, lesion smoothness, and lesion shape.

BRIEF DESCRIPTION OF THE DRAWING

The invention will be more fully understood from the following detailed description, in conjunction with the following figures, wherein.

DETAILED DESCRIPTION

Figure 1:
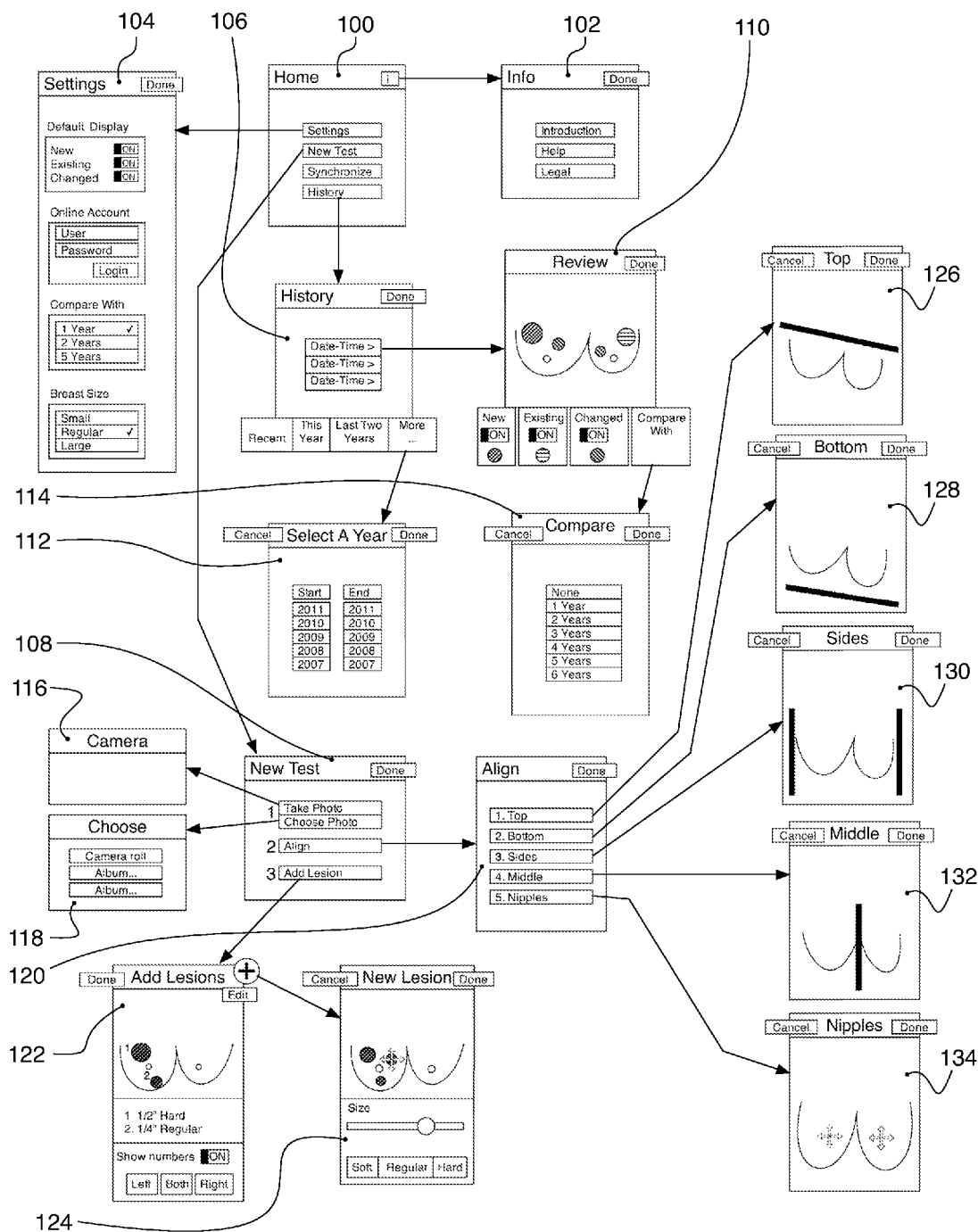
FIG. 1 is a top-level overview of all user interface screens, the various options in each screen and the paths that a user can take when navigating among the screens.

To conduct a breast self-examination using the method of the invention, a woman takes a frontal picture of her breasts, preferably while lying on her back, using a digital camera that can transfer the picture into a processing device. The processing device can be a personal computer, or a smart-phone, or a dedicated custom-built device. The digital camera can also be an integral part of the processing device, such as in the case of an iPhone™. The processing device will normalize the picture, enable the device operator to enter graphical as well as textual information, and store the final data set for visualization and comparative analysis.

Data Storage

Data sets can be stored directly on the processing device (such as a personal computer, iPhone™, etc.), on an attached storage device (such as a hard disk attached directly to a personal computer or a network shared storage device), on a properly configured web/cloud storage device, or on a dedicated web service.

Privacy and Security

User accounts on all storage devices will be anonymous and contain no personally identifiable information. Furthermore, none of the actual pictures will be stored. Data stored will be limited to normalized coordinates and properties of the findings, with no information linking the data to an individual. Access to the data sets will be controlled by means of user-selected username and password.

Image Alignment

Each image is aligned and normalized according to the following procedure:
1. Horizontally align the top of the breasts
   a. Operator aligns a reference line with the top of the breasts in the picture.
   b. Software rotates the image so that the top of the breasts is horizontal.
2. Normalize length of both breasts
   a. Operator aligns a reference line with the bottom of both breasts.
   b. Software performs a linear vertical stretch of the shorter breast so that the image of both breasts appears to be the same length.
3. Normalize picture width
   a. Operator aligns two vertical lines with the left and right edges of the breast image.
   b. Software performs a linear horizontal and vertical stretch of the picture so that the image of the breasts fills the assigned width or height, whichever is reached first. This type of scaling is often referred to as "fit to screen".
4. Normalize breast width
   a. Operator aligns a vertical line with the crease between the two breasts in the picture.

b. Software performs a linear horizontal stretch one breast and a linear horizontal compression the other breast, until the middle line is positioned in the middle of the picture.

5. Position both nipples
   a. Operator positions a separate graphical marker on each nipple.
   b. Software establishes the coordinate system
      i. Each nipple is at X, Y=0,0 (zero, zero)
      ii. Woman's left side of each breast is at X=+100
      iii. Woman's right side of each breast is at X=−100
      iv. Top of each breast is at Y=+100
      v. Bottom of each breast is at Y=−100

Coordinates

The method defines coordinates for each breast separately. 0,0 is at the center of each nipple.
Top of each breast is +100.
Bottom of each breast is −100.
Right side of each breast is +100.
Left side of each breast is −100.

Data Analysis

The method compares lesion position, size, and consistency.

Position comparison is based on normalized results, where coordinate values are between 0 and 100. Two lesions in two different result sets is considered as the same if their location is within a sensitivity range factor that can be defined by the user. The initial default will be set to 20.

Size comparison is based on user input. A lesion size is considered as changed when the difference between all measurements of the same lesion in all data sets being compared is larger than ¼ inch.

Consistency comparison is based on user input. Lesion consistency is considered as changed if there is a difference in consistency for the same lesion as recorded in all data sets being compared.

With reference to FIG. 1, this is a top-level view of all user interface screens. Breast examination application starts in the "Home" screen 100. From the "Home" screen 100, the user can navigate to the "Info" screen 102, or "Settings" screen 104, or "History" screen 106, or "New Test" screen 108. There is no recommended order in which the user would go through the various screens. Some screens will be used multiple times while others, such as the "Info" screen 102, may possibly never get used. All screens, except the "Home" screen 100, have a way of navigating back to the previous screen by touching a "Done" button. Touching the "Done" button saves all changes and/or accepts all selections before returning to previous screen. Some screens also have a "Cancel" button that cancels all changes and/or selections made before returning to the previous screen.

From the "History" screen 106, the user can navigate to "Review" screen 110, or "Select A Year" screen 112.

From "Review" screen 110, a user can navigate to "Compare" screen 114.

From "New Test" screen 108, the user can navigate to "Camera" screen 116 or "Choose" screen 118, and then to "Align" screen 120, and then "Add Lesions" screen 122.

From "Add Lesion" screen 122, the user can navigate to "New Lesion" screen 124.

From "Align" screen 120, the user can navigate to "Top" screen 126, or to "Bottom" screen 128, or to "Sides" screen 130, or to "Middle" screen 132, or to "Nipples" screen 134.

Figure 2:
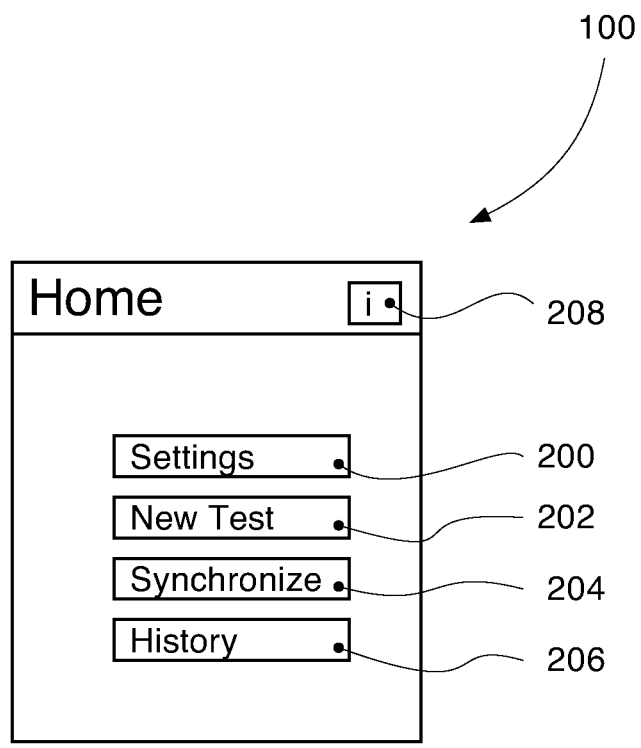
FIG. 2 is a schematic view of the "Home" screen with various buttons linking to other screens.

With reference to FIG. 2, this is a schematic view of the "Home" screen 100. Although the actual sequence in which any individual user touches the various buttons is a matter of personal preference, the natural sequence is "Settings" button 200, then "New Test" button 202, then optionally "Synchronize" button 204. After several uses of to the "New Test" button 202, the user may also start regularly using the "History" button 206. The user will once in a while, depending on personal preference, use the "i" button 208.

The "i" button 208 will be mostly utilized by novice users, with a diminishing frequency as users gain familiarity and experience with the software. "Synchronize" button 204 is the only button that does not lead to a screen but rather an action. It will initiate synchronization between locally stored data and corresponding data stored in a centralized data repository (not shown).

Figure 3:
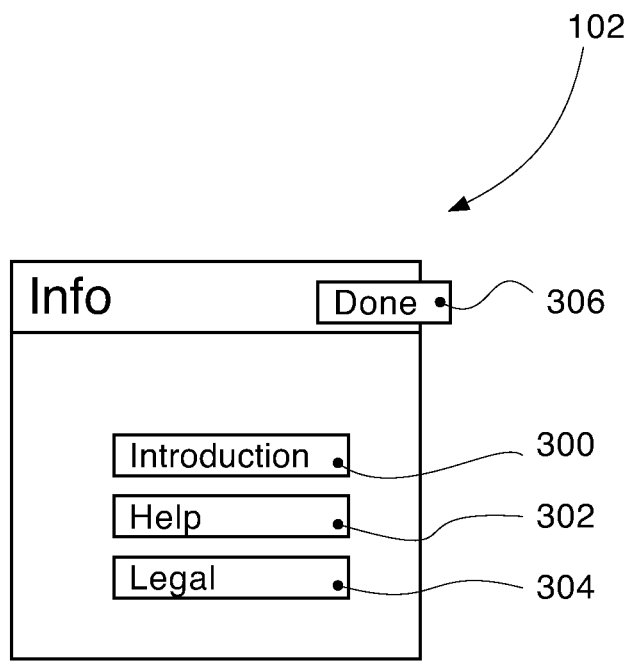
FIG. 3 is a schematic view of the "Info" screen, with various buttons linking to other screens, containing detailed information related to each button.

With reference to FIG. 3, this is a schematic view of the "Info" screen 102. Although the actual sequence in which any individual user touches the various buttons is a matter of personal preference, the natural sequence is "Introduction" button 300, then "Help" button 302, and then "Legal" button 304.

The "Introduction" button 300 displays a general introduction to the software and a general introduction to the subject matter of breast examination.

The "Help" button 302 displays text and graphical information, possibly organized in a hierarchical manner, explaining the various functionalities of this software and guidance as to the recommended way of using the software.

The "Legal" button 304 displays legal and regulatory information that may either be informational in nature, or required to be disclosed by law, or a matter of proper disclosure that would be beneficial to the users.

Figure 4:
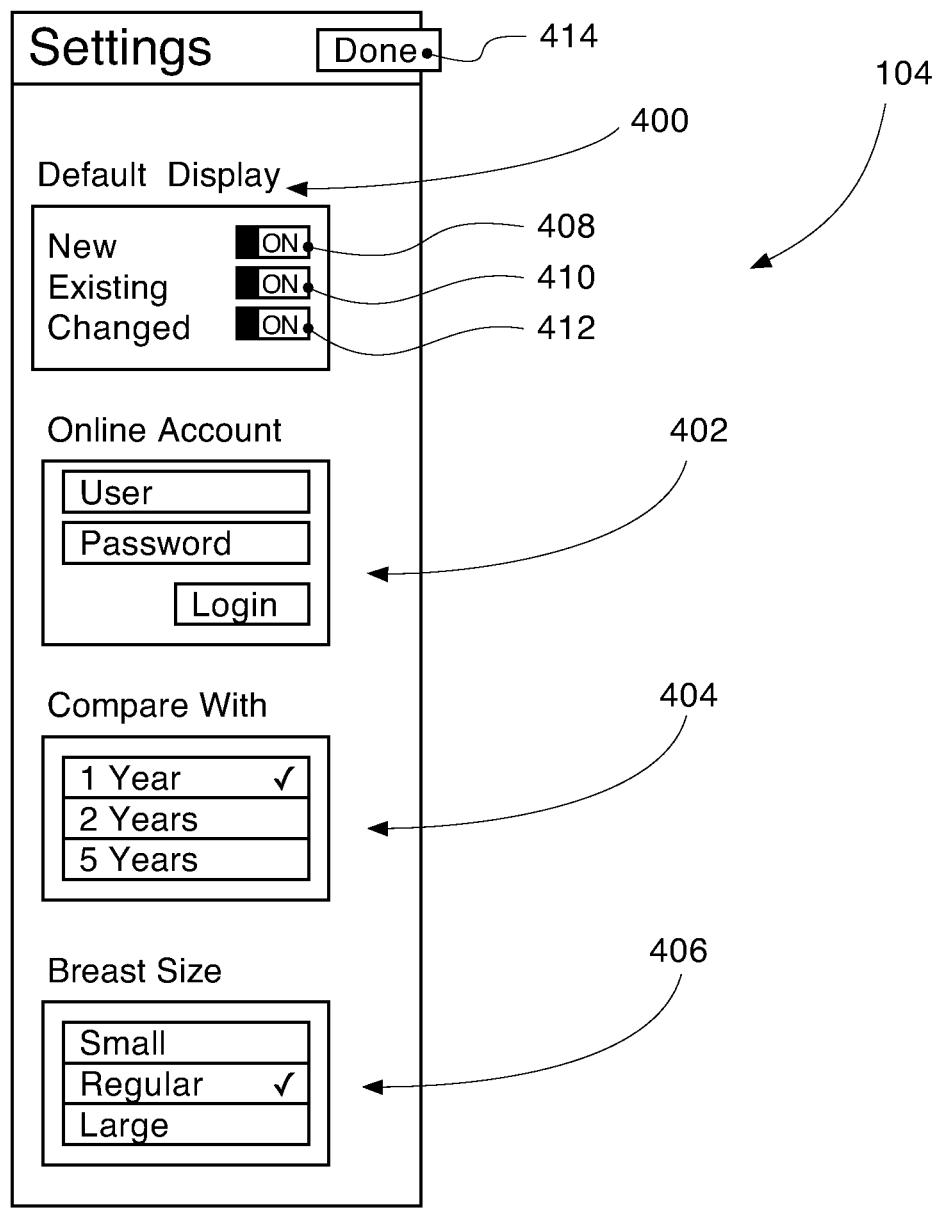
FIG. 4 is a schematic view of the "Settings" screen with various options that can be chosen or entered.

The "Done" button 306 returns the user to the "Home" screen 100. With reference to FIG. 4, this is a schematic view of the "Settings" screen 104. The actual sequence in which any individual user touches the various buttons and selects various options is a matter of personal preference and software user experience level. Information on this screen is arranged in functional groups "Default Display" group 400, "Online Account" group 402, "Compare With" group 404, and "Breast Size" group 406. The "Default Display" group 400 contains three on/off toggles that set what type of data is displayed on the screen. "New" toggle 408 toggles the display of new findings. "Existing" toggle 410 toggles the display of previously existing findings. "Changed" toggle 412 toggles the display of findings that changed.

The "Online Account" group 402 contains credentials for use when logging into an online repository, for synchronization and backup.

The "Compare With" group 404 contains an options wheel for selecting the default comparison range.

The "Breast Size" group 406 contains an options wheel for choosing an estimate for examined breast size.

The "Done" button 414 returns the user to the "Home" screen 100.

Figure 5:
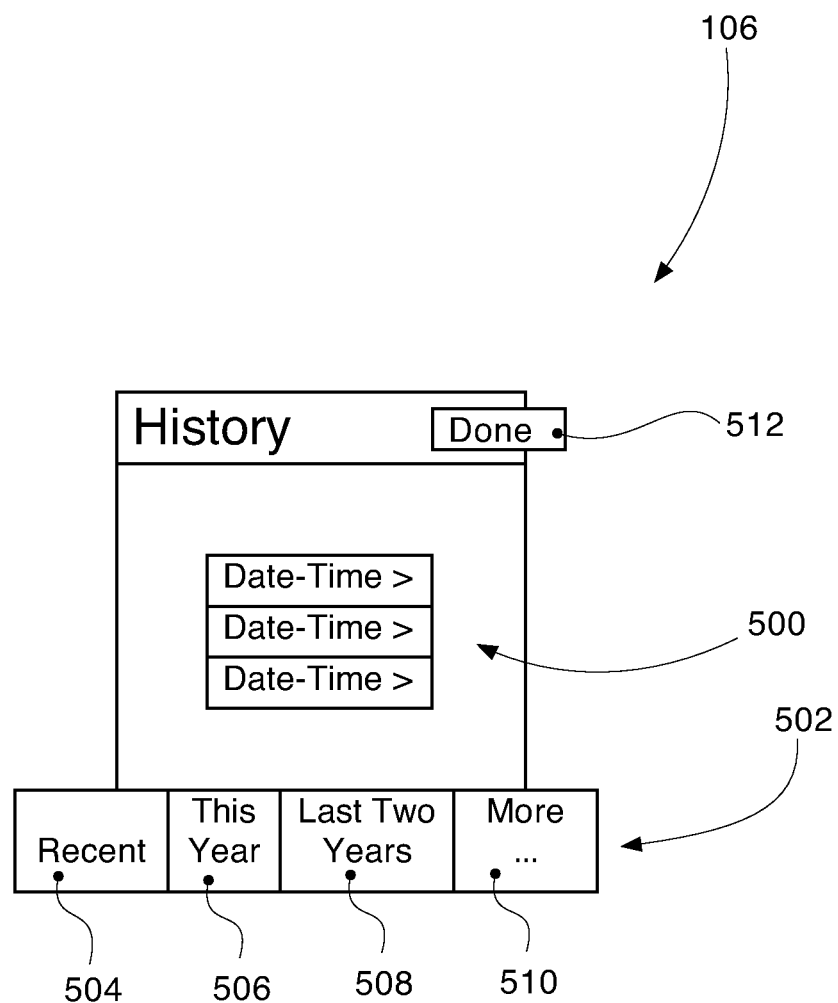
FIG. 5 is a schematic view of the "History" screen with various options that can be chosen.

With reference to FIG. 5, this is a schematic view of the "History" screen 106. Options wheel 500 contains a list of available historical data. Option buttons 502 on the bottom of the screen define the scope of available historical data. The "Recent" option button 504 selects ten most resent data sets. The "This Year" option button 506 selects all data sets from the current calendar year. The "Last Two Years" option button 508 selects all data sets from the two previous calendar years. The "More" option button 510 opens the "Select A Year" screen 112.

Selecting an option from the options wheel 500 links to the "Review" screen 110 that displays the selected data set.

The "Done" button 512 returns the user to the "Home" screen 100.

Figure 6:
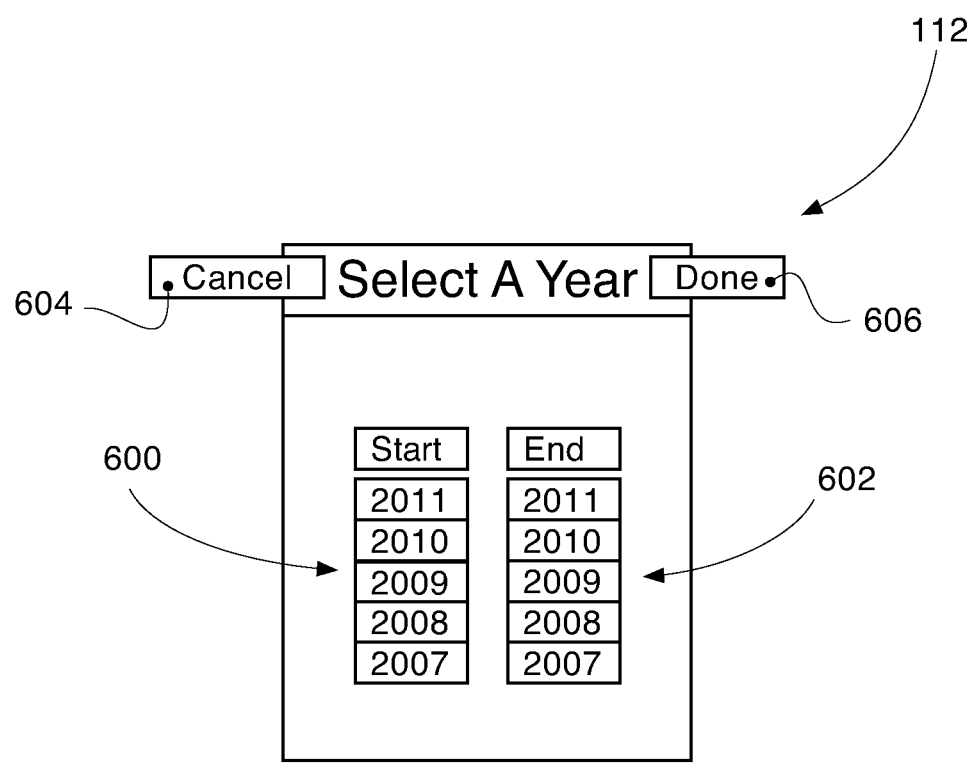
FIG. 6 is a schematic view of the "Select A Year" screen with various options that can be chosen.

With reference to FIG. 6, this is a schematic representation of the "Select A Year" screen 112. Option wheel 600 is used to specify the start year. Option wheel 602 is used to specify the end year. "Cancel" button 604 is used to cancel the selection and to return to the previous screen. "Done" button 606 accepts the selected year range and returns control to the original screen that caused the "Select A Year" screen 112 to appear.

Figure 7:
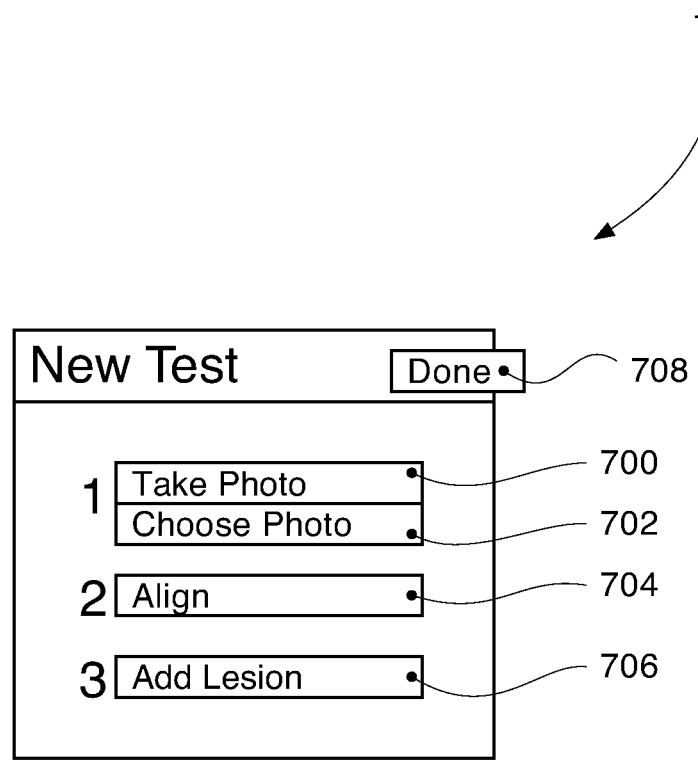
FIG. 7 is a schematic view of the "New Test" screen with various options that can be chosen.

With reference to FIG. 7, this is a schematic representation of the "New Test" screen 108. "Take Photo" button 700 links to standard camera screen 116, as implemented by the device used, such as an iPhone®. "Choose Photo" button 702 links to the standard photo selection screen 118, as implemented by the device used to implement the invention. "Align" 704 links to the "Align" screen 120. "Add Lesion" 706 links to the "Add Lesion" screen 122. "Done" button 708 closes the screen and returns control to the "Home" screen 100.

The "New Test" 108 screen will be used in a predefined sequence. First the user needs to acquire an image of a woman's breast by either taking a snapshot using a camera or by importing an existing image. "Take Photo" 700 is used to take a snapshot. "Choose Photo" 702 is used to import an existing image. Second, the user needs to use "Align" 704 to normalize the image of the breasts. Finally, "Add Lesion" is used to mark lesions on the image of the breasts.

Figure 8:
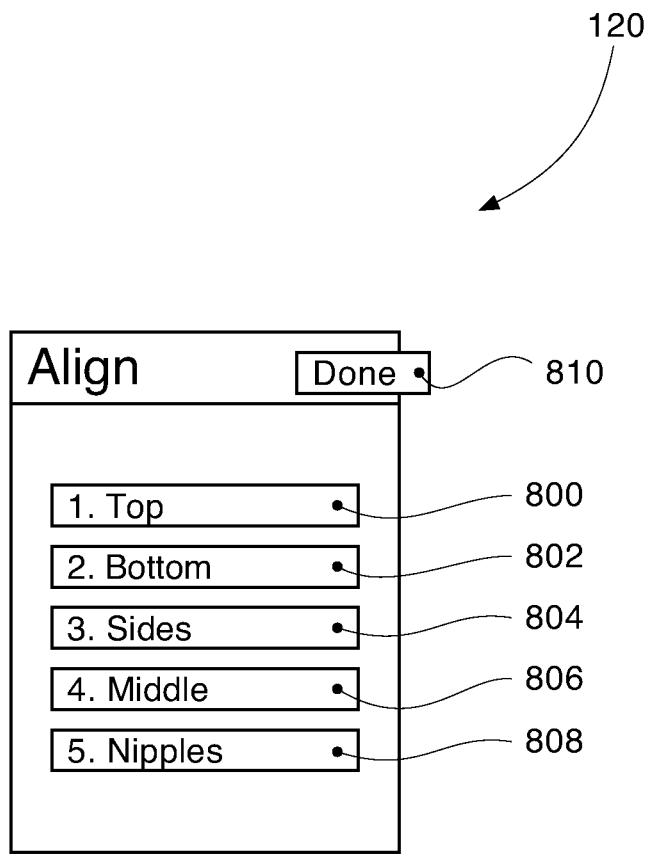
FIG. 8 is a schematic view of the "Align" screen with various options that can be chosen.

With reference to FIG. 8, this is a schematic representation of the Alignment screen 120. Button top 800 links to the top alignment screen 126. Button bottom 802 links to the bottom alignment screen 128. Button sides 804 links to the sides alignment screen 130. Button middle 806 links to the sides alignment screen 130. Button middle 806 links to the middle alignment screen 132. Button nipples 808 links to the nipples alignment screen 134. Done button 810 closes the screen and returns control to the home screen 100.

Figure 9:
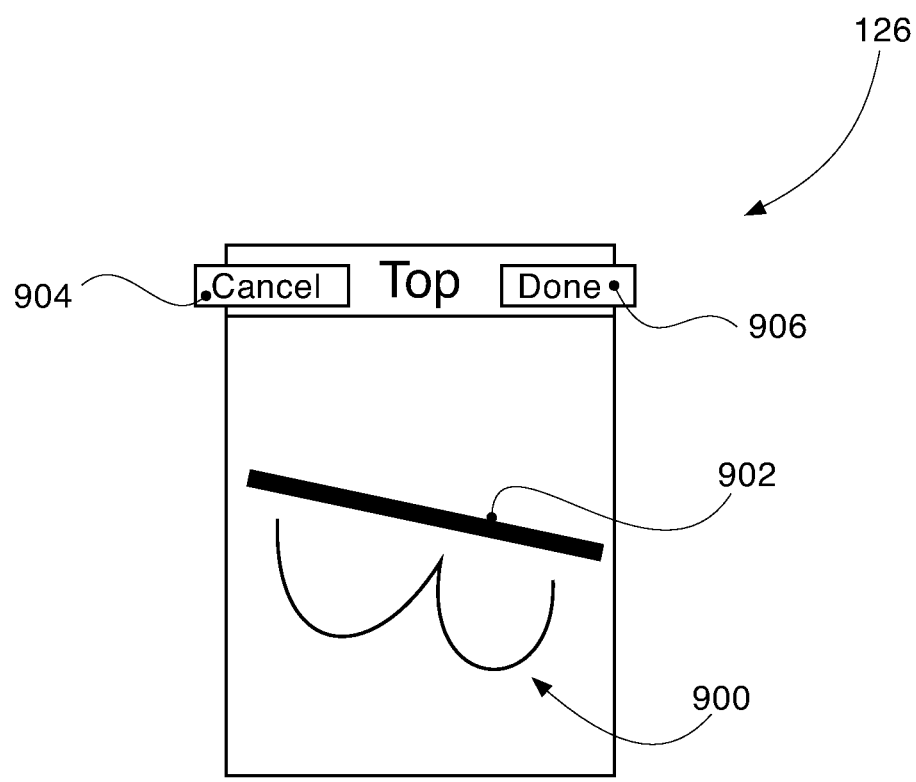
FIG. 9 is a schematic view of the "Top" screen with various options that can be chosen.

With reference to FIG. 9, this is a schematic representation of the "Top" screen 126. An image of woman's breasts 900 is overlaid with a line 902. User will utilize standard iPhone touch finger swipes to position line 902 along the top edge of the two breasts in image 900. The line 902 will need to be positioned such that the line 902 is connecting the topmost point of each breast. The line 902 does not need to be horizontal. Touching "Cancel" 904 will cancel all actions and return the user to the "Align" screen 120. Touching "Done" 906 will accept the marking of the top and return the user to the "Align" screen 120.

Figure 10:
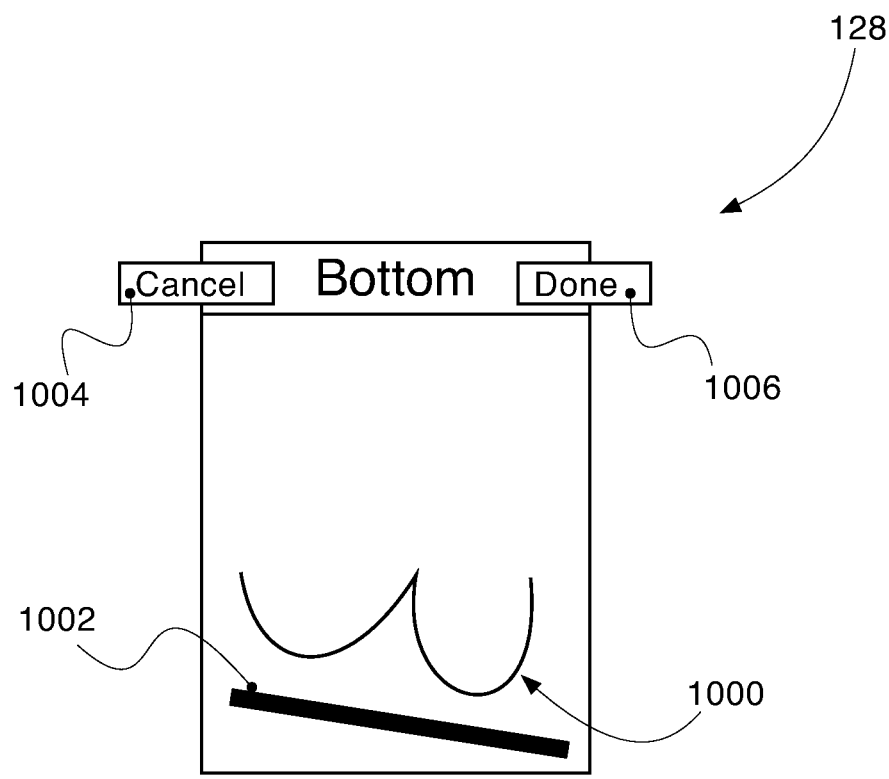
FIG. 10 is a schematic view of the "Bottom" screen with various options that can be chosen.

With reference to FIG. 10, this is a schematic representation of the "Bottom" screen 128. An image of woman's breasts 1000 is overlaid with a line 1002. User will utilize standard iPhone touch finger swipes to position line 1002 along the bottom edge of the two breasts in image 1000. The line 1002 will need to be positioned such that the line 1002 is touching each breast at a single point only. Typically, the line 1002 will not be horizontal. Touching "Cancel" 1004 will cancel all actions and return the user to the "Align" screen 120. Touching "Done" 1006 will accept the marking of the bottom and return the user to the "Align" screen 120.

Figure 11:
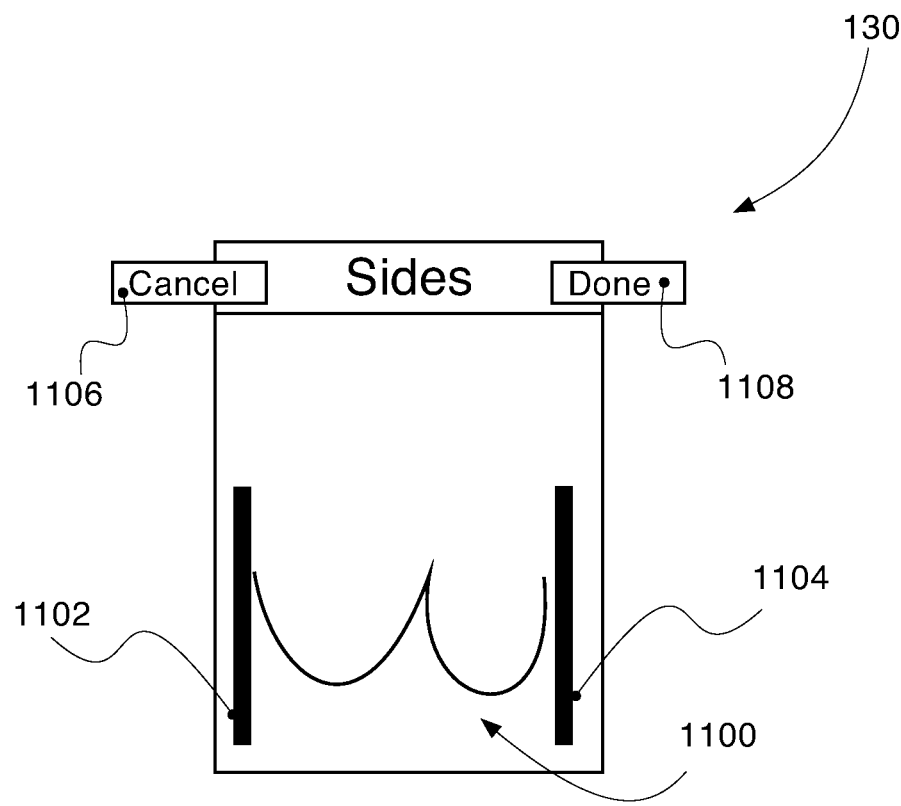
FIG. 11 is a schematic view of the "Sides" screen with various options that can be chosen.

With reference to FIG. 11, this is a schematic representation of the "Sides" screen 130. An image of woman's breasts 1100 is overlaid with a left vertical sideline 1102 and a right vertical sideline 1104. User will utilize standard iPhone touch finger swipes to position the left vertical sideline 1102 along the leftmost point of the two breasts in image 1100 and the right vertical sideline 1104 along the rightmost point of the two breasts image 1100. Touching "Cancel" 1106 will cancel all actions and return the user to the "Align" screen 120. Touching "Done" 1108 will accept the markings of the left and right sides and return the user to the "Align" screen 120.

Figure 12:
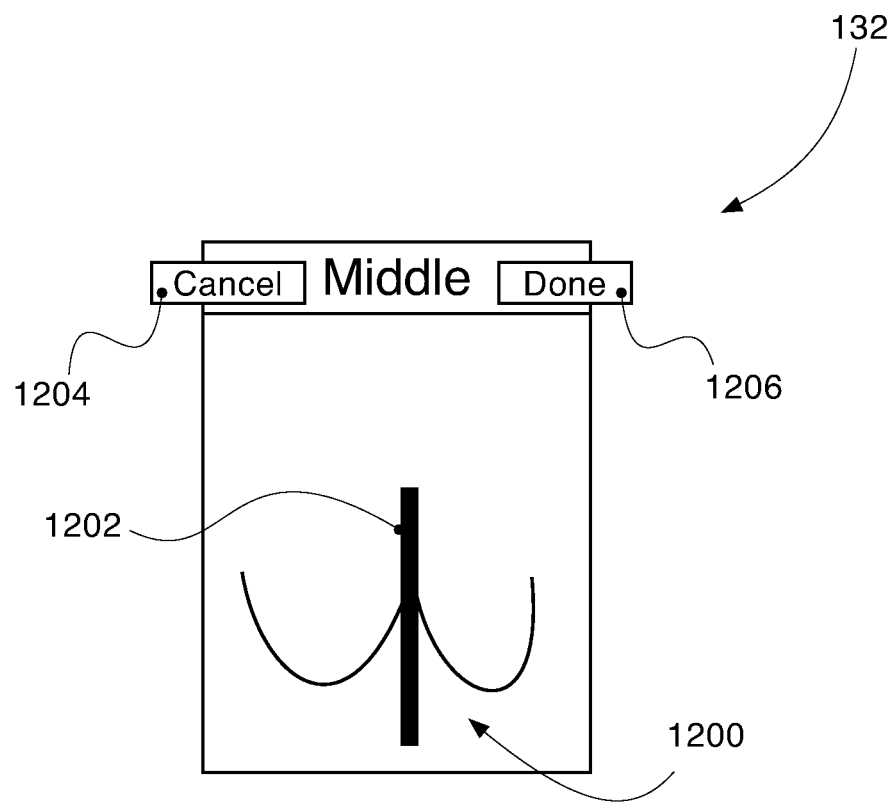
FIG. 12 is a schematic view of the "Middle" screen with various options that can be chosen.

With reference to FIG. 12, this is a schematic representation of the "Middle" screen 132. An image of woman's breasts 1200 is overlaid with a vertical line 1202. User will utilize standard iPhone touch finger swipes to position line 1202 at the center of the middle crease between the two breasts in image 1200. Touching "Cancel" 1204 will cancel all actions and return the user to the "Align" screen 120. Touching "Done" 1206 will accept the marking of the middle and return the user to the "Align" screen 120.

Figure 13:
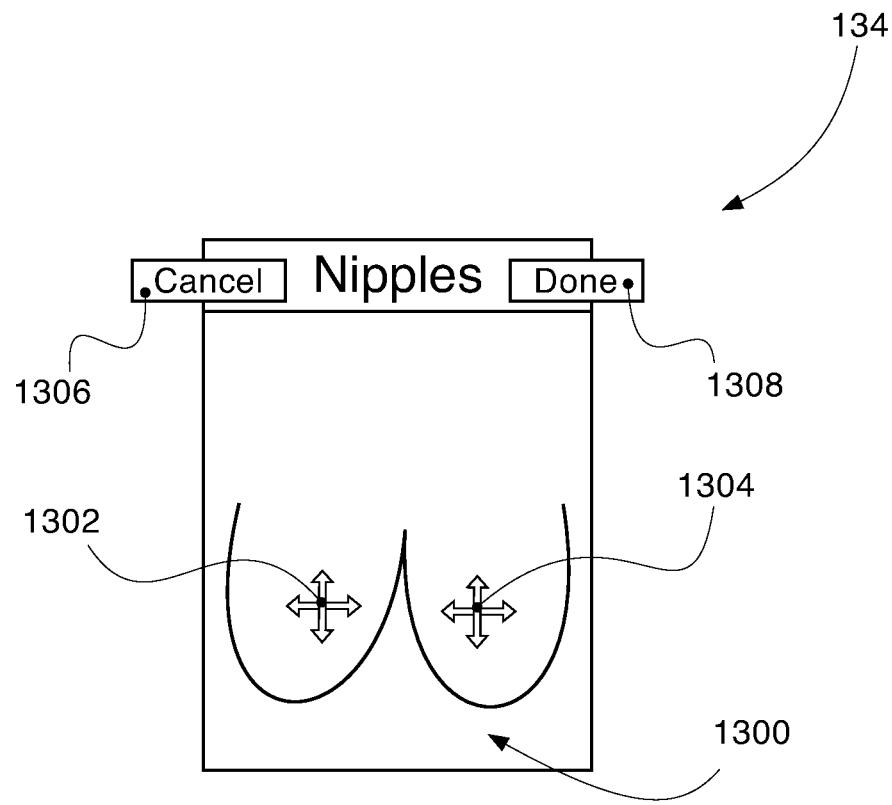
FIG. 13 is a schematic view of the "Nipples" screen with various options that can be chosen.

With reference to FIG. 13, this is a schematic representation of the "Nipples" screen 134. An image of woman's breasts 1300 is overlaid with a left nipple marker 1302 and a right nipple marker 1304. User will utilize standard iPhone touch finger swipes to position the center of the left nipple marker 1302 over the center of the left nipple in the image 1300 and the center of the right nipple marker 1304 over the center of the right nipple in the image 1300. Touching "Cancel" 1306 will cancel all actions and return the user to the "Align" screen 120. Touching "Done" 1308 will accept the markings of the left and the right nipples and return the user to the "Align" screen 120.

Figure 14:
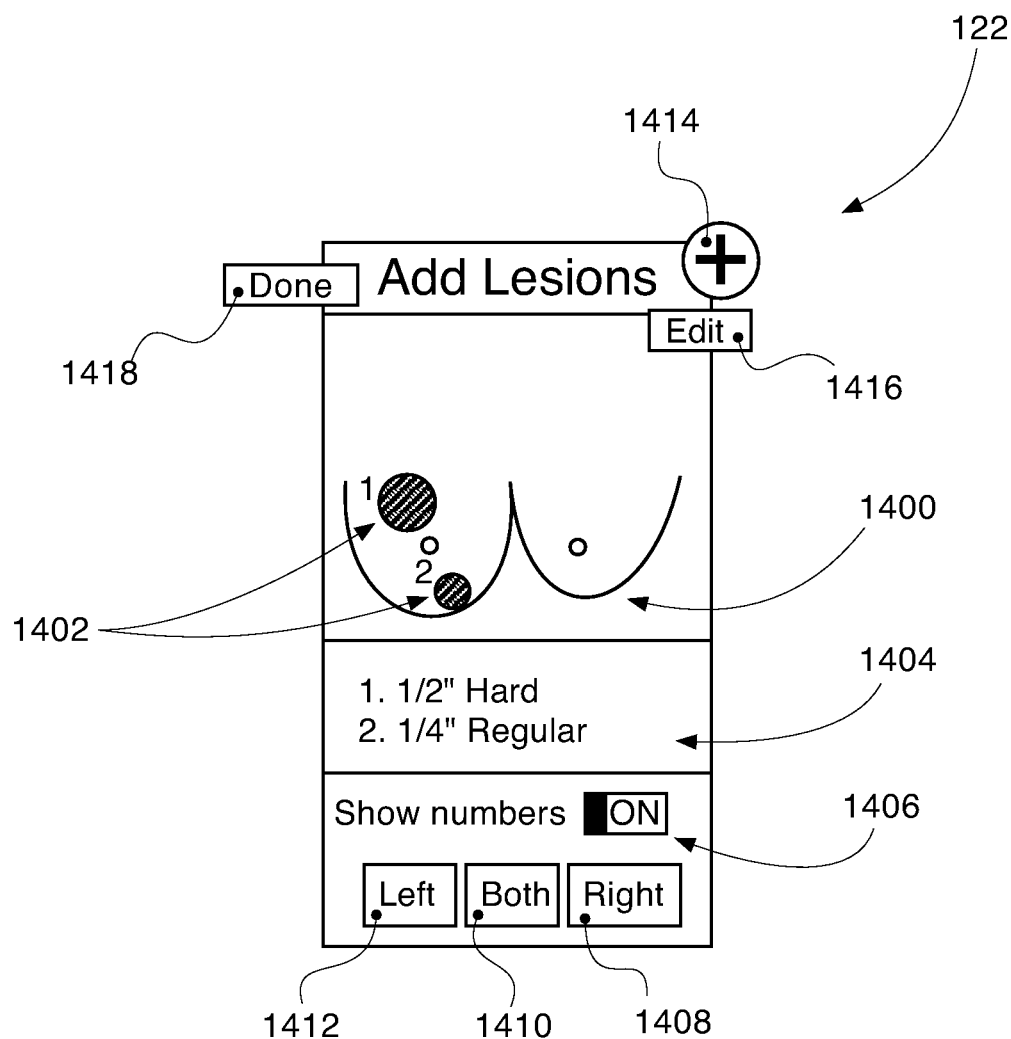
FIG. 14 is a schematic view of the "Add Lesions" screen with various options that can be chosen.

With reference to FIG. 14, this is a schematic representation of the "Add Lesions" screen 122. An image of a woman's breasts 1400 is overlaid with a plurality of lesion markers 1402. Summary information about each lesion marked is also displayed in a scrolling region 1404. "Show numbers" toggle 1406 can toggle display of lesion numbers next to the lesion graphical representation 1402. Touching button "Right" 1408 will display only the right breast. Touching button "Both" 1410 will display both breasts. Touching button "Left" 1412 will display only the left breast. "+" button 1414 links to "New Lesion" screen 124. "Edit" button 1416 enables deleting lesions by selecting the lesions to be deleted in the scrolling region 1404. Touching "Done" 1418 will return the user to the "New Test" screen 108.

Figure 15:
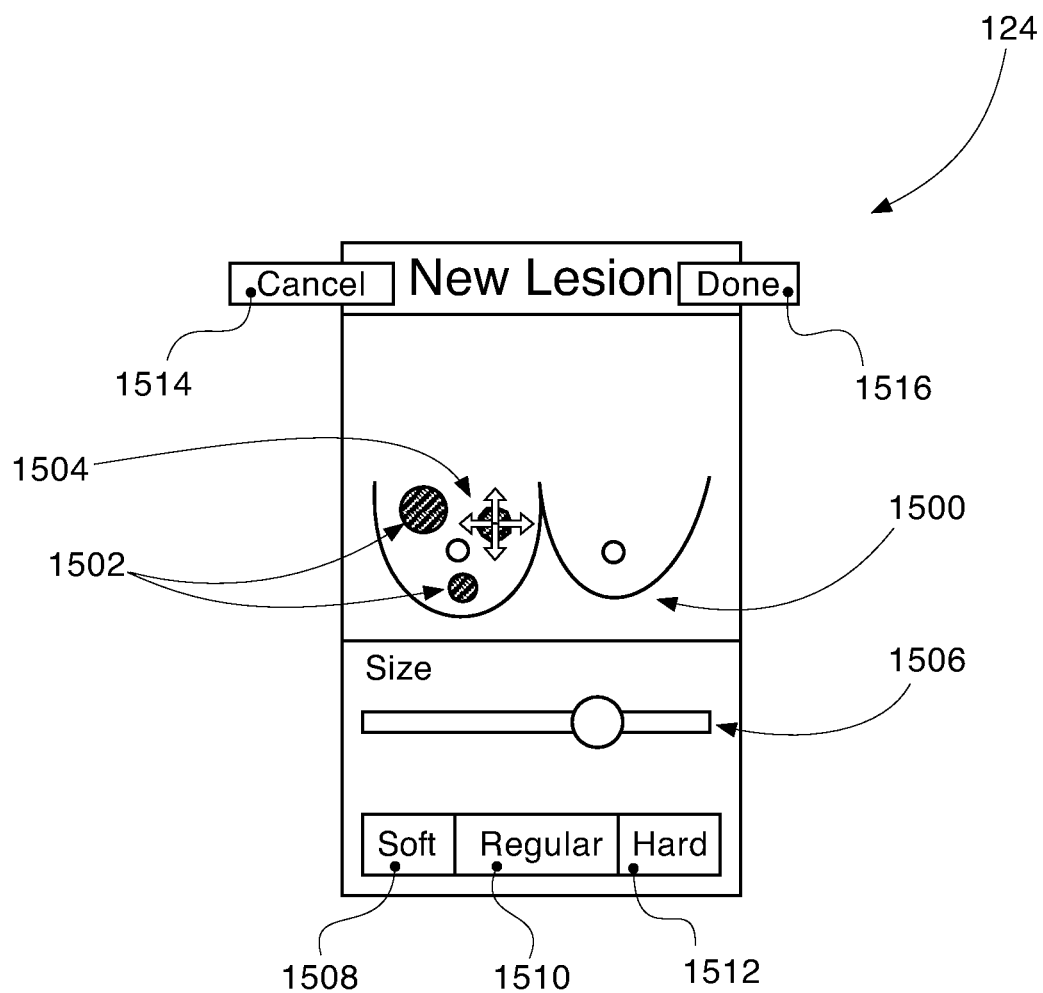
FIG. 15 is a schematic view of the "New Lesion" screen with various options that can be chosen and controls that can be operated.

With reference to FIG. 15, this is a schematic representation of the "New Lesion" screen 124. An image of a woman's breasts 1500 is overlaid with a plurality of existing lesion markers 1502. Using standard finger touch and swipe motions, user positions a new lesion marker 1504. Slider 1506 is used to indicate lesion size and option buttons "Soft" 1508, "Regular" 1510 and "Hard" 1512 are used to indicate lesion hardness. Touching "Cancel" 1514 will cancel all actions and return the user to the "Add Lesions" screen 122. Touching "Done" 1516 will accept the new lesion and return the user to the "Add Lesions" screen 122.

Figure 16:
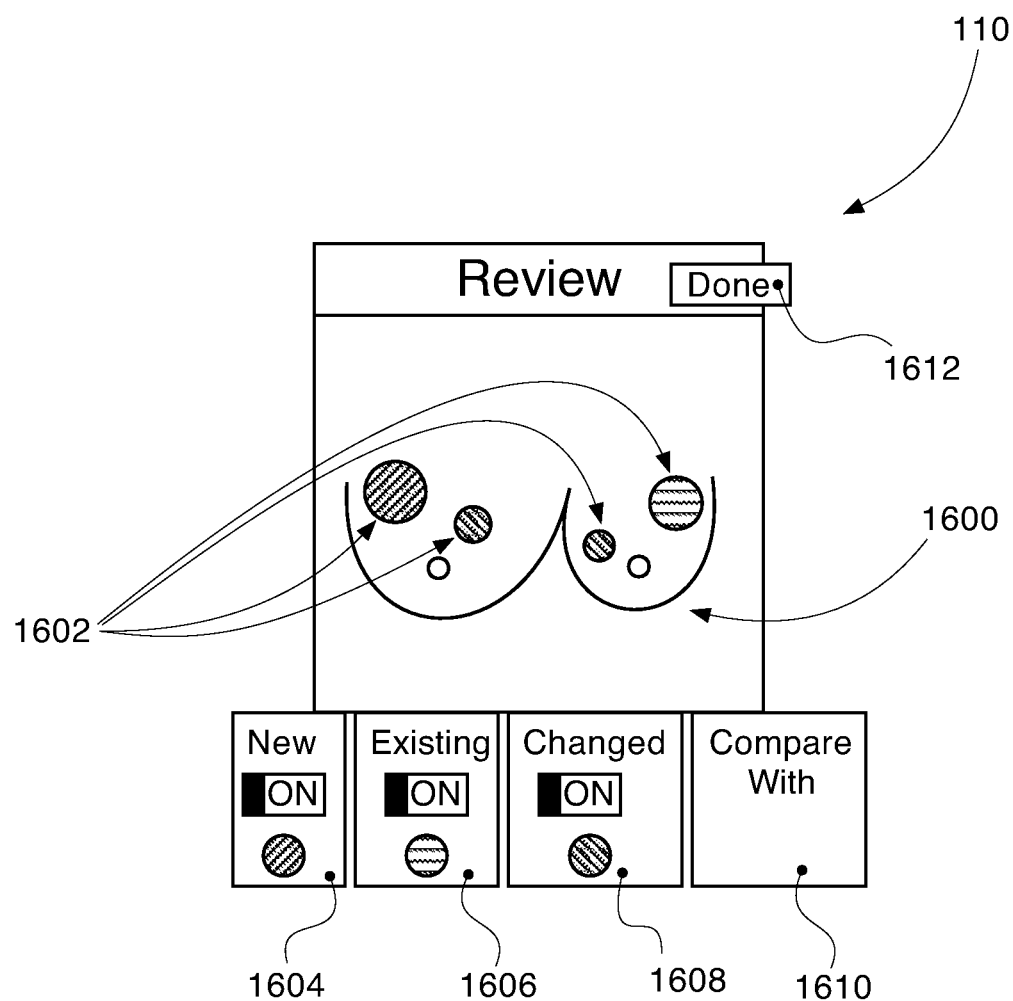
FIG. 16 is a schematic view of the "Review" screen with various options that can be chosen and controls that can be operated.

With reference to FIG. 16, this is a schematic representation of the "Review" screen 110. An image of a woman's breasts 1600 is overlaid with a plurality of new, existing, and changed lesion markers 1602. "New" toggle 1604 toggles the display of lesion markers that represent new lesions. "Existing" toggle 1606 toggles the display of lesion markers that exist in history. "Changed" toggle 1608 toggles the display of lesion markers that exist in history but have changed in size or hardness. The "Compare With" button 1610 links to the "Compare" screen 114. Touching "Done" 1612 returns the user to the "History" screen 106.

Figure 17:
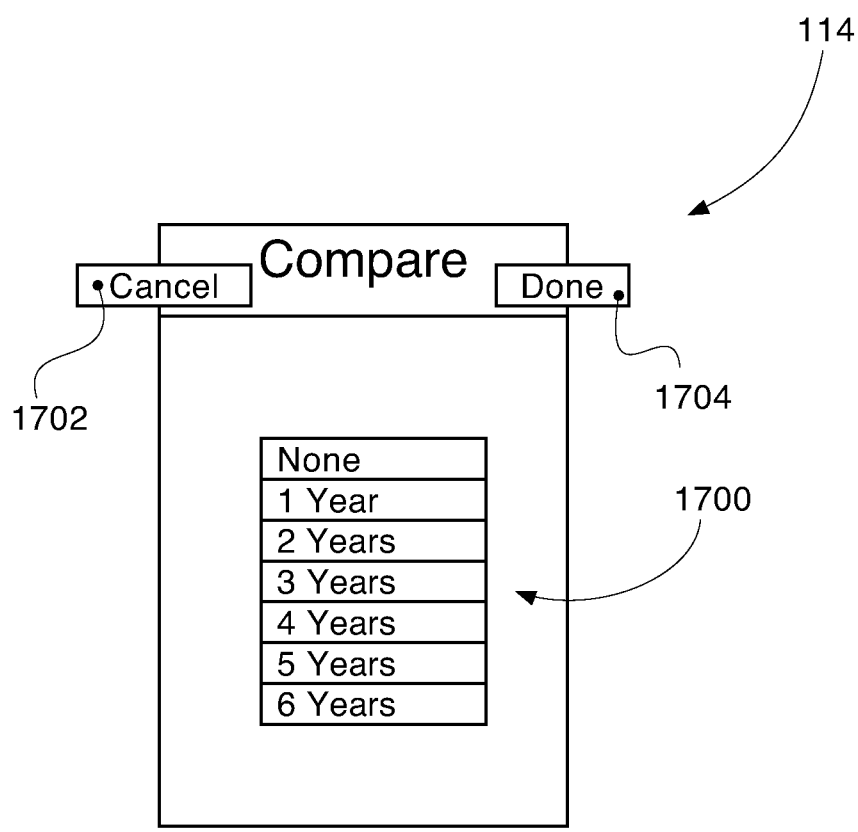
FIG. 17 is a schematic view of the "Compare" screen with various options that can be chosen.

With reference to FIG. 17, this is a schematic representation of the "Compare" screen 114. Options wheel 1700 enables selection of comparison period. Touching "Cancel" 1702 cancels selection and returns the user to the "Review" screen 110. Touching "Done" 1704 accepts the comparison period and returns the user to the "Review" screen 110.

Other modifications and implementations will occur to those skilled in the art without departing from the spirit and the scope of the invention as claimed. Accordingly, the above description is not intended to limit the invention, except as indicated in the following claims.

What is claimed is:

1. A computer software product for enabling mapping and recording of breast examination results, the computer software product having computer readable program code that is stored on a non-transitory memory medium, the computer readable program code being capable of being accessed from the non-transitory memory medium by a processing device, the accessed program code adapted to be executed by the processing device to perform a method comprising:

enabling visible characterization of found lesions in a digital image of a woman's breasts, the visible characterization indicating breast lesion information including at least one of: lesion location, lesion consistency, lesion smoothness, lesion shape;

determining a breast coordinate system for each breast, the breast coordinate system for each breast having a respective coordinate system origin;

mapping the location of each found lesion into a respective breast coordinate system so as to provide coordinates of each found lesion;

enabling digital recording of the coordinates of each found lesion along with other breast lesion information; and normalizing the digital image using the breast coordinate system so as to provide a normalized digital image, wherein normalizing the digital image using the breast coordinate system includes:

rotating the digital image so as to horizontally align the tops of the two breasts;

angularly distorting the digital image by extending the shorter breast so as to horizontally align the bottoms of the two breasts, thereby making the two breasts appear to be of identical length;

expanding digital image width to fit the image of the two breasts to a pre-determined width;

expanding digital image height to fit the image of the two breasts to a pre-determined height; and equalizing width of each of the two breasts within the digital image of the two breasts.

2. The computer software product of claim 1, wherein determining a breast coordinate system for each breast for use in lesion mapping includes:

enabling finding-each nipple within the digital image so as to provide nipple position information for each nipple.

3. The computer software product of claim 1, wherein determining a breast coordinate system for each breast for use in lesion mapping includes:

enabling determination of a top breast pair boundary line, a bottom breast pair boundary line, a left breast boundary line, a center line between the breasts, and a right breast boundary line within the digital image so as to provide a set of reference lines.

4. The computer software product of claim 1, wherein the method further comprises:

retrieving breast lesion information.

5. The computer software product of claim 1, wherein the method further comprises:

comparing breast lesion information between at least two different data sets of breast lesion information, those data sets resulting from two different examinations of the woman's breasts.

6. The computer software product of 1, wherein the method further comprises:

for each breast, distorting the digital image of each breast vertically and horizontally, without changing height and width of the digital image of each breast, so as to locate each nipple at the coordinate system origin of each breast.

7. The computer software product of claim 1, wherein the method further comprises:

enabling presentation of normalized breast lesion information results from a breast examination on a representation of a breast.

8. The computer software product of claim 1, wherein the method further comprises:

enabling presentation of breast lesion information resulting from at least one prior breast examination.

9. The computer software product of claim 1, wherein the method further comprises:

enabling presentation of breast lesion information representation marks that are color-coded so as to indicate breast lesion characteristics.

10. The computer software product of claim 1, wherein enabling visible characterization of found lesions in a digital image of a woman's breasts includes:

automatically detecting marks made by the woman directly on her breasts to indicate locations of lesions using image processing; and automatically relating the marks to the coordinate system of the image.

11. A computer software product for enabling mapping and recording of breast examination results, the computer software product having computer readable program code that is stored on a non-transitory memory medium, the computer readable program code being capable of being accessed from the non-transitory memory medium by a processing device, the transferred program code adapted to be executed by the processing device to perform a method comprising:

enabling visible characterization of found lesions in a digital image of a woman's breasts, the visible characterization indicating breast lesion information including at least one of: lesion location, lesion consistency, lesion smoothness, lesion shape;

determining a breast coordinate system for each breast, the breast coordinate system for each breast having a respective coordinate system origin;

mapping the location of each found lesion into a respective breast coordinate system so as to provide coordinates of each found lesion wherein said mapping further includes:

defining an origin as (0,0) for each breast, and positioning each origin at the position of a nipple of each breast in the representation of the breast;

defining the left side of each breast to be at X=−100 within the coordinate system, the scale of the left side of each breast being independent from the scale of the left side of the other breast;

defining the right side of each breast to be at X=+100 within the coordinate system, the scale of the right side of each breast being independent from the scale of the right side of the other breast, and the scale of the right side of each breast being independent from the scale of the left side of the same breast;

defining the bottom side of each breast to be at Y=−100 within the coordinate system, the scale of the bottom side of each breast being independent from the scale of the bottom side of the other breast, and independent of all scales in X; and defining the top side of each breast to be at Y=+100 within the coordinate system, the scale of the top side of each breast being independent from the scale of the top side of the other breast, and the scale of the top side of each breast being independent from the scale of the bottom side of the same breast, and independent of all scales in X; and enabling digital recording of the coordinates of each found lesion along with other breast lesion information.

12. A computer implemented method for mapping and recording breast examination results, the method comprising:

providing visible characterization of found lesions in a digital image of a woman's breasts, the visible characterization indicating breast lesion information including at least one of: lesion location, lesion consistency, lesion smoothness, lesion shape;

determining a breast coordinate system for each breast, the breast coordinate system for each breast having a respective coordinate system origin;

mapping the location of each found lesion into a respective breast coordinate system to provide coordinates of each found lesion;

digitally recording the coordinates of each found lesion along with other breast lesion information; and normalizing the digital image using the breast coordinate system to provide a normalized digital image, wherein normalizing the digital image using the breast coordinate system includes:

rotating the digital image to horizontally align the tops of the two breasts;

angularly distorting the digital image by extending the shorter breast to horizontally align the bottoms of the two breasts, thereby making the two breasts appear to be of identical length;

expanding digital image width to fit the image of the two breasts to a pre-determined width;

expanding digital image height to fit the image of the two breasts to a pre-determined height; and equalizing width of each of the two breasts within the digital image of the two breasts.

13. The computer implemented of claim 12, wherein said determining a breast coordinate system for each breast for use in lesion mapping includes locating each nipple within the digital image to provide nipple position information for each nipple.

14. The computer implemented of claim 12, wherein said determining a breast coordinate system for each breast for use in lesion mapping includes determining a top breast pair boundary line, a bottom breast pair boundary line, a left breast boundary line, a center line between the breasts, and a right breast boundary line within the digital image to provide a set of reference lines.

15. The computer implemented of claim 12, further comprising retrieving breast lesion information.

16. The computer implemented of claim 12, further comprising comparing breast lesion information between at least two different data sets of breast lesion information, those data sets resulting from two different examinations of the woman's breasts.

17. The computer implemented of claim 12, further comprising for each breast, distorting the digital image of each breast vertically and horizontally, without changing height and width of the digital image of each breast, to locate each nipple at the coordinate system origin of each breast.

18. The computer implemented of claim 12, further comprising presenting normalized breast lesion information results from a breast examination on a representation of a breast.

19. The computer implemented of claim 12, further comprising presenting breast lesion information resulting from at least one prior breast examination.

20. The computer implemented of claim 12, further comprising presenting breast lesion information representation marks that are color-coded to indicate breast lesion characteristics.

* * * * *